US006923422B2

(12) United States Patent
Schmaltz

(10) Patent No.: US 6,923,422 B2
(45) Date of Patent: Aug. 2, 2005

(54) VALVE FOR CONTROLLING FLUID FLOW THROUGH A TUBE, AND RELATED SYSTEMS AND METHODS

(76) Inventor: Ronald Anthony Schmaltz, 23702 3rd Pl. West, Bothell, WA (US) 98021

( * ) Notice: Subject to any disclaimer, the term of this patent is extended or adjusted under 35 U.S.C. 154(b) by 0 days.

(21) Appl. No.: 10/807,776

(22) Filed: Mar. 23, 2004

(65) Prior Publication Data

US 2004/0178375 A1 Sep. 16, 2004

Related U.S. Application Data

(63) Continuation of application No. 10/116,571, filed on Apr. 3, 2002, now Pat. No. 6,814,337.

(51) Int. Cl.[7] .................................................. F16K 7/04
(52) U.S. Cl. ......................................... 251/7; 251/294
(58) Field of Search ............................... 251/7, 8, 294; 4/480; 74/500.5, 500.2, 519, 523, 526, 527, 532, 535, 501.6

(56) References Cited

U.S. PATENT DOCUMENTS

| | | |
|---|---|---|
| 355,741 A | 1/1887 | Reinmann |
| 358,026 A | 1/1887 | Boyden |
| 1,322,421 A | 11/1919 | French |
| 2,167,952 A | 8/1939 | Jordan |
| 2,841,357 A | 7/1958 | Little |
| 3,044,466 A | 7/1962 | Henderson |
| 3,415,299 A | 12/1968 | Hinman, Jr. et al. |
| 3,807,453 A | 4/1974 | Dorn et al. |
| 3,931,650 A | 1/1976 | Miller |
| 4,172,580 A | 10/1979 | Raftis et al. |
| 4,262,876 A | 4/1981 | Willatt |
| 4,624,663 A | 11/1986 | Danby et al. |
| 4,667,778 A | 5/1987 | Ozaki |
| 4,702,733 A | 10/1987 | Wright et al. |
| 4,878,646 A | 11/1989 | Edelman et al. |
| 5,092,856 A | 3/1992 | Johnston |
| 5,265,840 A | 11/1993 | Gillespie et al. |
| 5,280,938 A | 1/1994 | Berry |
| 5,397,315 A | 3/1995 | Schmidt et al. |
| 5,584,596 A | 12/1996 | Greene |
| 6,012,181 A | 1/2000 | Johnson et al. |
| 6,024,257 A | 2/2000 | Djavit |
| 6,213,140 B1 | 4/2001 | Ploeger |
| 6,361,016 B1 | 3/2002 | Schulz |
| 6,526,603 B1 | 3/2003 | Murphy |

FOREIGN PATENT DOCUMENTS

| | | |
|---|---|---|
| DE | 19511469 | 10/1996 |
| GB | 646167 | 11/1950 |
| WO | WO 02/04849 A1 | 1/2002 |

OTHER PUBLICATIONS

International Search Report PCT/US 03/05932.

*Primary Examiner*—Edward K. Look
*Assistant Examiner*—John K. Fristoe, Jr.
(74) *Attorney, Agent, or Firm*—Graybeal Jackson Haley LLP

(57) ABSTRACT

A valve assembly for controlling the flow of fluid through a tube by pinching the tube to prevent fluid flow. The valve assembly includes a valve that receives the tube in a passage between a plunger and a bar. A spring urges the plunger toward the bar to pinch the tube closed. The bar focuses the pinching force of the plunger to reduce the pinching force required to prevent fluid flow. The valve assembly also includes a caliper for opening, locking open and closing the valve and that is attached to the valve with a cable. To open and close the valve, a main lever and lock lever, respectively are rotated in the same direction.

8 Claims, 3 Drawing Sheets

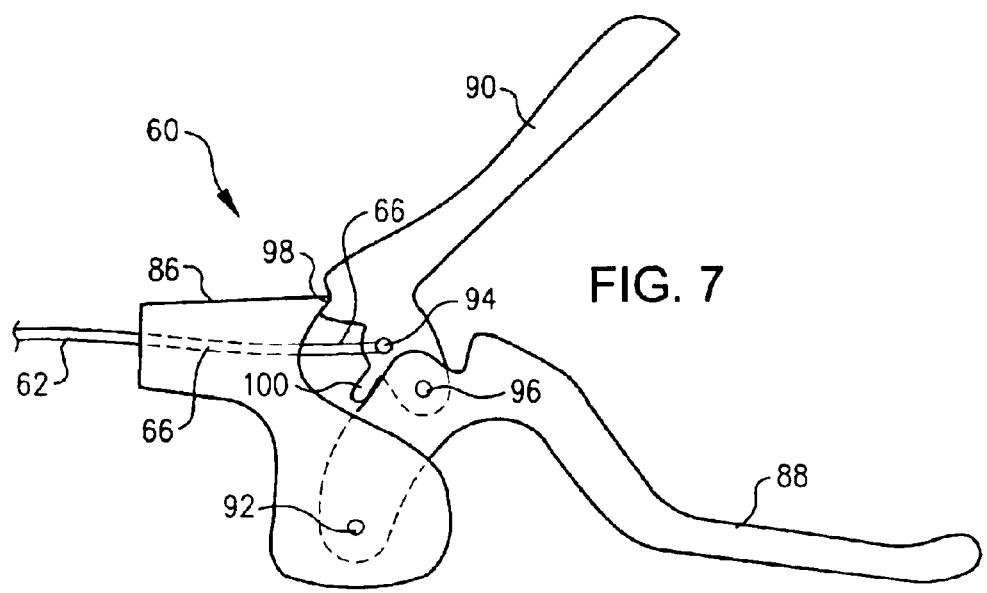
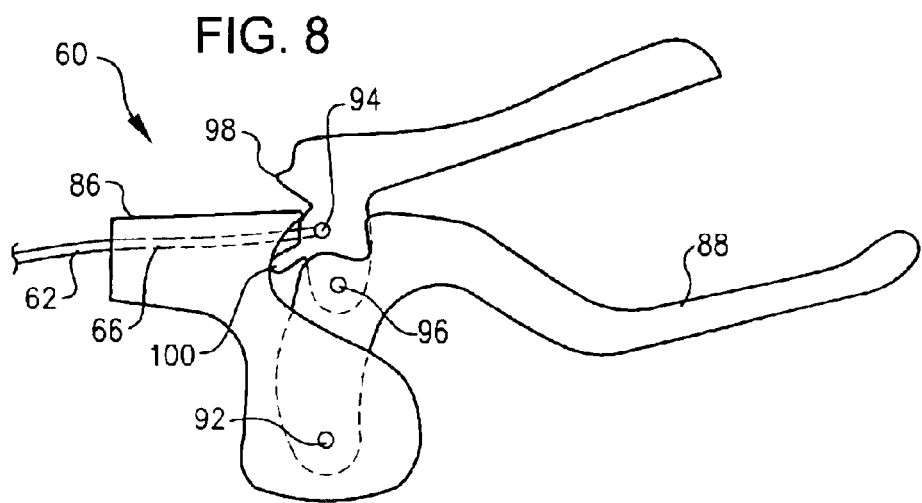
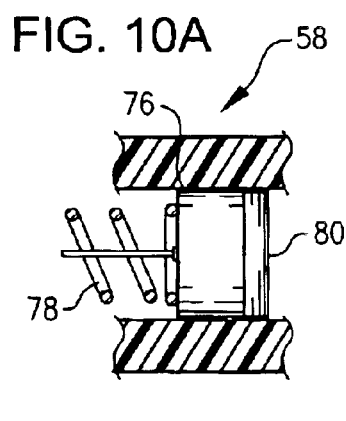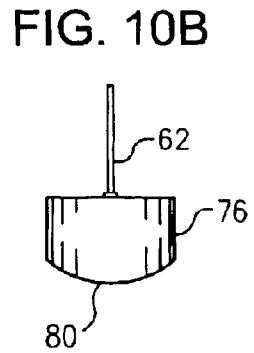

VALVE FOR CONTROLLING FLUID FLOW THROUGH A TUBE, AND RELATED SYSTEMS AND METHODS

This application is a continuation application of U.S. patent application Ser. No. 10/116,571 filed 3 Apr. 2002, now U.S. Pat. No. 6,814,337 the benefit of the filing date of which is claimed under 35 U.S.C. §120, and which is incorporated herein by reference.

BACKGROUND

Unfortunately, many people require the assistance of a drainage system to remove fluids such as urine from their body. For example, a quadriplegic typically has no control over his/her own bladder and depends on a drainage system to remove urine and allow him/her to venture away from a restroom for extended periods of time. The drainage system stores fluids and allows a user to dispose of these fluids at a time convenient for the user.

FIG. 1 shows a conventional drainage system 20, described in U.S. Pat. No. 5,092,856 to Johnston, that includes a reservoir 22 for storing a fluid and a valve 24 to control the flow of fluid from the reservoir. FIG. 2 shows a cross section of the valve 24 in FIG. 1 in a closed position. The drainage system 20 also includes a catheter 26 for transferring fluid to the reservoir 22 a drain tube 28 for transferring fluid out of the reservoir 22 and a lever 30 for selectively opening and closing the valve 24. To drain the reservoir 22, one opens the valve 28 by moving the lever 30. To quit draining the reservoir 22, one closes the valve 28 by releasing the lever 30.

The valve 24 includes a spring 32 that biases the valve in a closed position. The spring 32 forces the plunger 34 toward the end 36 to pinch the drain tube 28 closed. To insure that the drain tube 28 is sufficiently pinched to prevent flow through the tube 28 when the valve 24 is closed, the spring exerts considerable force on the plunger 34. Consequently, to open the valve 24 and keep it open while the reservoir drains, a user must overcome the spring's force on the plunger 34.

Unfortunately, the strength and dexterity required to open and keep open the valve typically exceeds a quadriplegic's strength and dexterity. To assist the quadriplegic, electrically controlled and operated valves can be used. But, their use presents other problems. First, such valves require a power source, which can be expensive to maintain and can expire at a very inconvenient time. Second, if the valve fails for some reason, for example water or other types of fluid damage the valve or power source, the valve may stick in the open or closed position. Stuck in the open position, the valve will not allow the drainage system to store fluids for any length of time. And stuck in the closed position, the valve will not allow the drainage system to be drained without permanently opening the valve.

Thus, there is a need for a valve to control the flow of fluid from a reservoir, that requires minimal force and dexterity to open, keep open, and close, and remains closed when not operated by a user.

SUMMARY

The present invention provides a valve assembly for controlling the flow of a fluid through a tube. The valve assembly requires minimal strength and dexterity to operate and thus can be operated by a user lacking these. The valve assembly includes a valve that can be opened and closed to permit, or prevent or substantially prevent fluid from flowing through the tube. The valve assembly also includes a caliper for selectively opening, keeping open and closing the valve. When closed, a spring in the valve forces a plunger to pinch the tube against a bar. The bar focuses the pinching force of the plunger and thus reduces the force required for the spring to close the valve. The caliper is attached to the valve by a cable and includes a main lever for opening the valve and a lock lever for keeping the valve open. Thus, a user does not have to "hold" the valve open. To open and close the valve, the main lever and lock lever, respectively, are rotated in the same direction. Thus, a user who can extend his/her arm with sufficient strength to open the valve yet cannot retract their arm with the same strength, can operate the valve.

BRIEF DESCRIPTION OF THE FIGURES

FIG. 7 is a side view of a caliper according to an embodiment of the invention, that is incorporated in the valve assembly in FIG. 3 and shown in the locked position.

FIG. 8 is a side view of the caliper in FIG. 7 in the unlocked position.

FIG. 10A is a cross-sectional view of a portion of a valve according to yet another embodiment of the invention that incorporates a plunger different than the plunger incorporated in the valves shown in FIGS. 4, 5, 9A and 9B.

FIG. 10B is a plan view of the plunger shown in FIG. 10A.

DETAILED DESCRIPTION

All terms used herein, including those specifically described below in this section, are used in accordance with their ordinary meanings unless the context or definition indicates otherwise. Also, unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

The present invention provides a valve assembly that controls the flow of a fluid through a tube. The valve assembly includes a valve that can receive a tube, can be opened to permit fluid to flow through the tube and can be closed to prevent or substantially prevent the fluid from flowing through the tube. In the closed position, the valve pinches the tube between a plunger and a bar to seal or substantially seal the portion of the tube upstream from the valve from the portion of the tube downstream from the valve. The bar focuses the pinching force of the plunger into a small area on the drain tube. Consequently, the pinching force of the valve can be minimized. In the open position, the valve partially pinches or does not pinch the tube to allow the seal to be broken and fluid to flow through the tube. The valve assembly also includes a caliper that one can operate to open, to lock open and to close the valve. By minimizing the pinching force and locking the valve open, a person having marginal strength and/or dexterity can open, keep open and close the valve. Thus, quadriplegics or other persons suffering from a lack of bladder control and reduced strength and/or dexterity in their limbs can easily operate the valve assembly to drain fluids such as urine from an external reservoir. Furthermore, because the valve is not electrically operated or controlled, the valve remains closed when not operated by a user.

Figure 1:
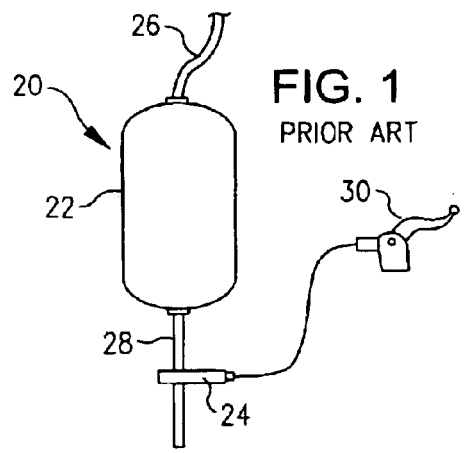
FIG. 1 is a schematic view of a conventional drainage system that includes a reservoir and valve.
Figure 3:
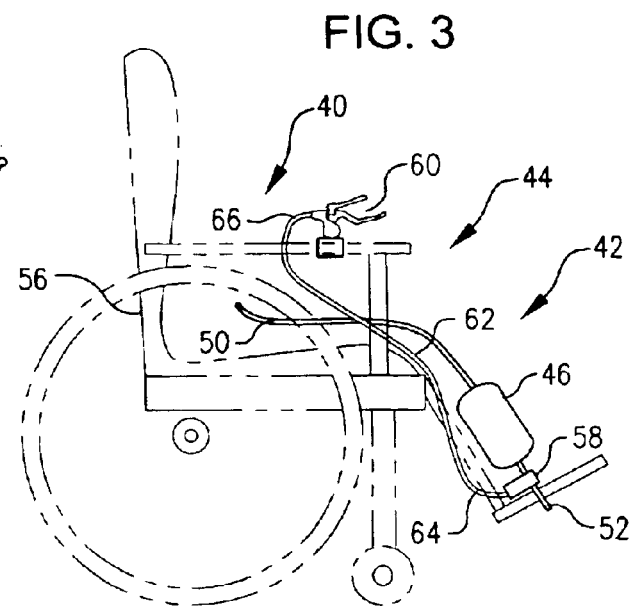
FIG. 3 is a side view of a drainage system incorporating a valve assembly according to an embodiment if the invention.
Figure 2:
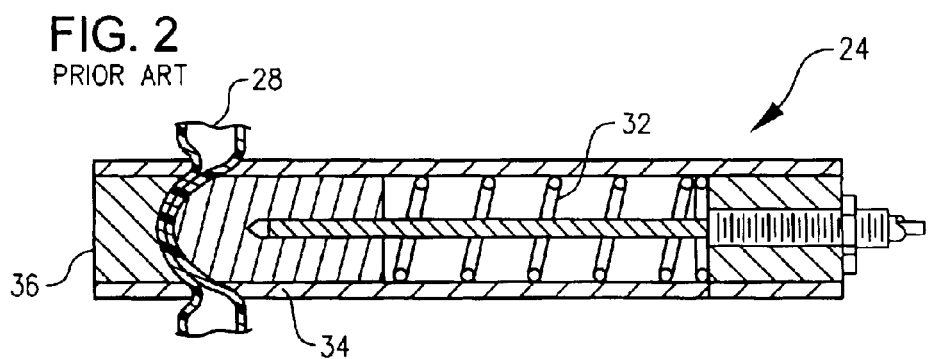
FIG. 2 is a cross-sectional view of a conventional valve incorporated in the system of FIG. 1.

FIG. 3 is a side view of a wheelchair 40 that includes a valve assembly 44 according to an embodiment of the invention. In this and certain other embodiments, the wheelchair 40 also includes a reservoir 46 for storing fluid generated by a user, a catheter 50 for transferring fluid from the user to the reservoir 46, and a drain tube 52 for draining the fluid from the reservoir 46. The valve assembly 44 controls the flow of fluid through the drain tube 52 and includes a valve 58 that can be opened and closed to permit or prevent urine from flowing through the drain tube 52, a caliper 60 for opening, locking open and closing the valve 58, and a cable 62 connecting the caliper 60 to the valve 58. The caliper 60 can be mounted on the wheelchair 40 using any desired fastening technique such as bolts and nuts, adhesive or Velcro® and at any desired location that facilitates the user's operation of the caliper 60. For example, the caliper 60 can be mounted on the frame 56 near the person's hand. In other embodiments, the caliper 60 can be mounted near the user's head if the user lacks strength and dexterity in either hand or either arm. The valve 58 can be mounted to the drain tube 52 or frame 56 of the wheelchair 40 using any desired technique. For example, in this embodiment the valve 58 is frictionally mounted to the drain tube 52 as discussed in greater detail elsewhere herein. In other embodiments, however, the valve 58 can be mounted to the wheelchair 40 in a similar manner as the caliper 60.

Still referring to FIG. 3, in this and certain other embodiments, the cable 62 is similar to a bicycle brake cable that transmits the motion of a brake handle squeezed by a rider to the brake pads of a wheel of the bicycle. More specifically, the cable 62 includes wound metal wires (not shown) that pass through a sheath (not shown). When the user operates the caliper 60, the wound metal wire slides inside the sheath and pulls on the valve 58. The cable 62 also includes a valve end 64 attached to the valve 58 and a caliper end 66 attached to the caliper 60. These ends 64 and 66 can be attached to the valve 58 and caliper 60, respectively, using any desired fastening technique such as soldering or pivotally retaining a knob (not shown) on the ends 64 and 66 in a slot (not shown) in the valve 58 and caliper 60, respectively.

Still referring to FIG. 3, in this and certain other embodiments, the catheter 50 and drain tube 52 can be connected to the reservoir 46 using any desired fastening technique that adequately seals the catheter 50 and drain tube 52 to the reservoir 46. For example, the catheter 50 and drain tube 52 can be glued to the reservoir 46. The reservoir 46 can be attached anywhere as desired, such as on the person's leg 54 or on the frame 56 of the wheelchair 40 using any desired fastening technique. For example, the reservoir 46 can be strapped to a user's leg with a belt or placed in a cage attached to the frame 56 of the wheelchair 40.

Still referring to FIG. 3, in operation, a user monitors the level of fluid in the reservoir 46. When the user determines that the reservoir 46 should be emptied, he/she places the drain tube 52 over the receptacle he/she wants to transfer the fluid to. Next, the user opens and locks open the valve 58 by operating the caliper 60, as discussed in greater detail in conjunction with FIGS. 7 and 8. After draining the reservoir 46, the user closes the valve 58 by operating the caliper 60, also discussed in greater detail in conjunction with FIGS. 7 and 8.

Figure 4:
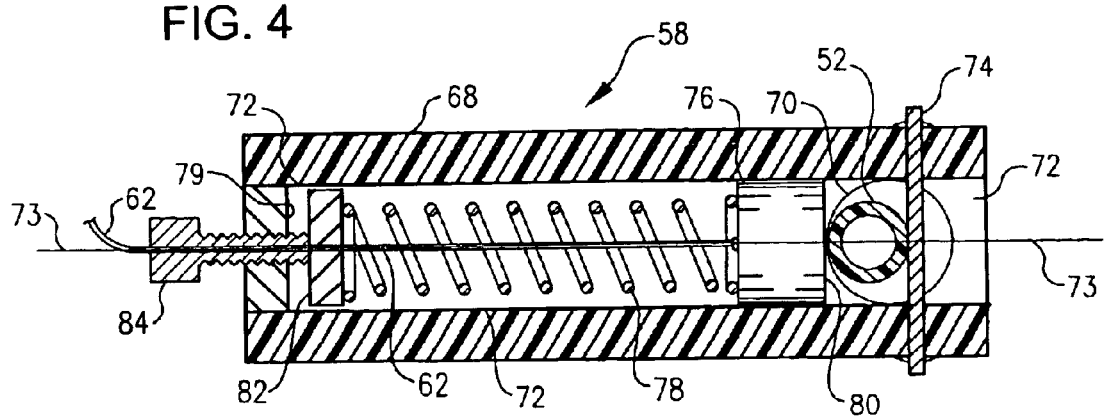
FIG. 4 is a cross sectional view of a valve according to an embodiment of the invention that is incorporated in the valve assembly in FIG. 3 and shown open.
Figure 5:
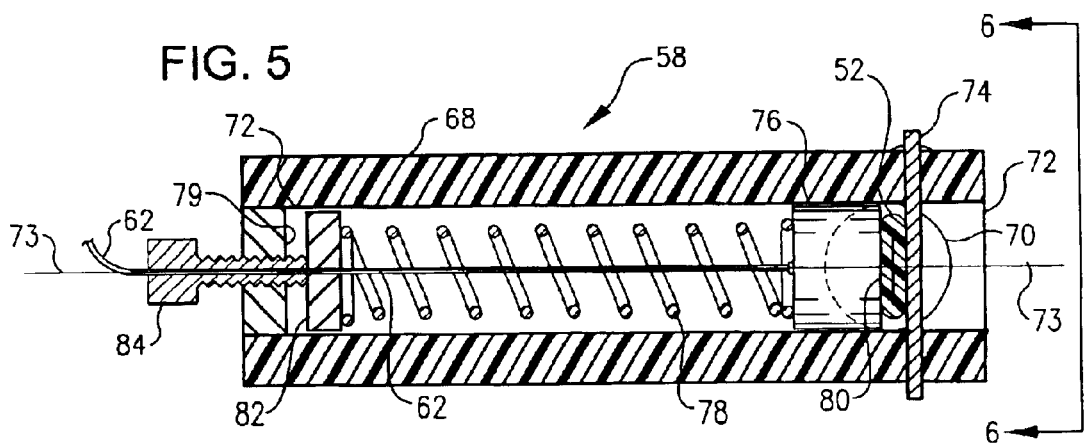
FIG. 5 is a cross-sectional view of the valve of FIG. 4 closed.

FIGS. 4 and 5 are cross-sectional views of the valve 58 in FIG. 3, according to an embodiment of the invention. FIG. 4 shows the valve 58 open to permit fluid to flow through the drain tube 52. FIG. 5 shows the valve 58 closed to prevent or substantially prevent fluid from flowing through the drain tube 52.

Referring to FIGS. 4 and 5, in this and certain other embodiments, the valve 58 includes a valve body 68 made from acrylonitrile butadiene styrene plastic (ABS) or, as desired, any other type of plastic or other material such as metal. The valve body 68 includes a passage 70 having a longitudinal axis 71 in FIG. 6 and sized to receive the drain tube 52, and a cavity 72 having a longitudinal axis 73. The passage 70 and cavity 72 intersect each other such that the longitudinal axes 71 and 73 are perpendicular or substantially perpendicular to each other. The valve 58 also includes a bar 74, a plunger 76 and a spring 78. The bar 74 extends perpendicular or substantially perpendicular to the longitudinal axis 71 and through the passage 70 and cavity 72 where the passage 70 and cavity 72 intersect. The plunger 76 is movable within the cavity 72 between an open and closed position. The spring 78 is disposed between a closed end 79 of the cavity 72 and the plunger 76 to bias the plunger 76 in the closed position. In the closed position, the spring 78 forces the plunger 76 toward the bar 74 to pinch a portion of the drain tube 52 between the plunger 76 and bar 74. When the plunger 76 is in the closed position the valve 58 is closed. In the open position, the plunger 76 is moved away from the bar 74 to allow the same portion of the drain tube 52 to expand, and the valve 58 is open. In addition, the plunger 76 and bar 74 remain in contact with the drain tube 52. Thus, the valve 58 remains connected to the drain tube 52 by friction. In other embodiments, such as when the valve 58 is attached directly to the wheelchair 40, the open position may not include the plunger 76 and bar 74 remaining in contact with the drain tube 52.

Still referring to FIGS. 4 and 5, the bar 74 focuses the pinching force in the plunger 76 to minimize the pinching force required to close the valve 58. In this and certain other embodiments, the bar 74 includes a straight, cylindrical or substantially cylindrical bar and focuses the pinching force to a straight or substantially straight line on the drain tube 52. The bar 74 has a diameter of two millimeters, is made of conventional stainless steel and is retained to the valve body 68 by friction. This allows one to quickly and easily remove the bar 74 to gain access to the whole cavity 72 or to replace the bar 74. In other embodiments, the bar 74 can have any diameter desired, be made from any desired material capable of providing enough rigidity to pinch the drain tube 52 when the plunger is in the closed position, and retained to the valve 58 by any desired fastener or fastening technique such as a snap ring or adhesive. In still other embodiments, the bar 74 can include a bar having any desired cross sectional shape such as a triangle or square.

Figure 9A:
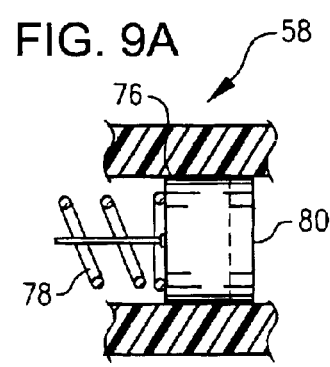
FIG. 9A is a cross-sectional view of a portion of a valve according to another embodiment of the invention that incorporates a plunger different than the plunger incorporated in the valve shown in FIGS. 4 and 5.
Figure 9B:
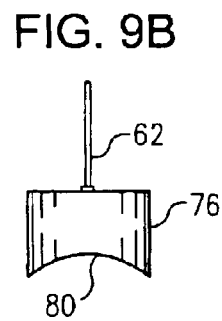
FIG. 9B is a plan view of the plunger shown in FIG. 9A.

Still referring to FIGS. 4 and 5, the plunger 76 moves within the cavity 72 to open and close the valve 58. In this and certain other embodiments, the plunger 76 is made of conventional stainless steel and includes a circular or substantially circular plate sized to slide within the cavity 72. The plunger 76 also includes a drain-tube-contact surface 80 that is flat or substantially flat. In other embodiments, the plunger 76 can be made of any desired material capable of providing enough rigidity to pinch the drain tube 52 closed when the plunger is in the closed position. Additionally or alternatively, the plunger 76 can be any desired shape such as a triangle or square that permits the plunger 76 to slide within the cavity 72. Additionally or alternatively, the plunger 76 can also include a drain-tube-contact surface 80 that is contoured. For example, the drain-tube-contact surface 80 can include a concave portion, as shown in FIGS. 9A and 9B, that matches the bar's shape or the surface 80 can include a convex portion, as shown in FIGS. 10a and 10B, that further focuses the pinching force in the plunger 76.

Still referring to FIGS. 4 and 5, the spring 78 biases the plunger 76 towards the bar 74. In this and certain other embodiments, the spring 78 includes a coil spring sized to be in compression when the plunger 76 is in the closed position. Furthermore, the spring 78 is sized to provide a minimal amount of force to the plunger 76 to pinch the drain tube 52 closed and close the valve 58. The spring 78 is made of conventional spring steel but can be made of any other desired material such as other kinds of steel or other metals. In other embodiments, the spring 78 may include any desired type of spring that can provide the pinching force required, such as a Belleville spring.

Still referring to FIGS. 4 and 5, to move the plunger 76 to the open position, one operates the caliper 60 in FIG. 3 as discussed in greater detail in conjunction with FIGS. 7 and 8. In the closed position, the spring 78 forces the plunger 76 toward the bar 74 to pinch the drain tube 52. To close the valve 58 the spring 78 must provide enough force to the plunger 76 to generate a seal between the collapsed portions of the drain tube 52. Operating the caliper 60 causes the cable 62 to pull the plunger 76 away from the bar 74. Thus, to move the plunger 76 away from the bar 74 the cable must provide more force than the spring 78.

Still referring to FIGS. 4 and 5, in this and certain other embodiments, the valve 58 also includes a spring adjustment plate 82 for adjusting the pinching force of the plunger 76 and a spring adjustment member 84 for moving and retaining the spring adjustment plate 82 in a desired position. The spring adjustment plate 82 is disposed in the cavity 72 of the valve body 68 between the closed end 79 and the spring 78. To adjust the pinching force of the spring 78, the spring adjustment plate 82 is movable toward or away from the closed end 79. The spring adjustment member 84 includes a screw threaded through the closed end 79. By rotating the screw, the spring adjustment plate 82 is moved toward or away from the closed end 79. To retain the spring adjustment plate 82, the plate 82 is compressed between the screw and the spring 78. In other embodiments, the valve 58 may not include a spring adjustment plate 82, and the spring 78 may be compressed between a shoulder of the spring adjustment member 84 and the plunger 76.

Still referring to FIGS. 4 and 5, adjustment of the pinching force may be required when a spring having a different spring constant is inserted into the cavity 72 of the valve body 68 or when a different drain tube 52 is inserted into the passage 70 of the valve 58. In addition, the spring adjustment member 84 and spring adjustment plate 82 can serve as an alternative means for opening and closing the valve 58 should the caliper 60 or cable 62 malfunction. For example, the spring can be sized to provide a pinching force when the spring adjustment plate 82 is located away from the closed end 79 and provide a pinching force insufficient to close the valve 58 when the plate 82 is located next to the closed end 79. To open the valve 58, one could rotate the spring adjustment member 84 out of the body 68. To close the valve 58 one could rotate the spring adjustment member 84 into the body 68.

Although the valve 58, as shown, includes one bar 74, the valve may include more than one bar. This may be desired when fluid pressure within the drain tube is high enough to require an excessive pinching force with one bar 74 to prevent or substantially prevent fluid from flowing through the drain tube 52. In addition, although the valve 58, as shown, receives one drain tube 52, the passage 70 can be sized to receive two or more drain tubes 52. Furthermore, although the valve 58, as shown, includes one spring 78, the valve 58 can include more than one spring 78 and more than one type of spring.

Figure 6:
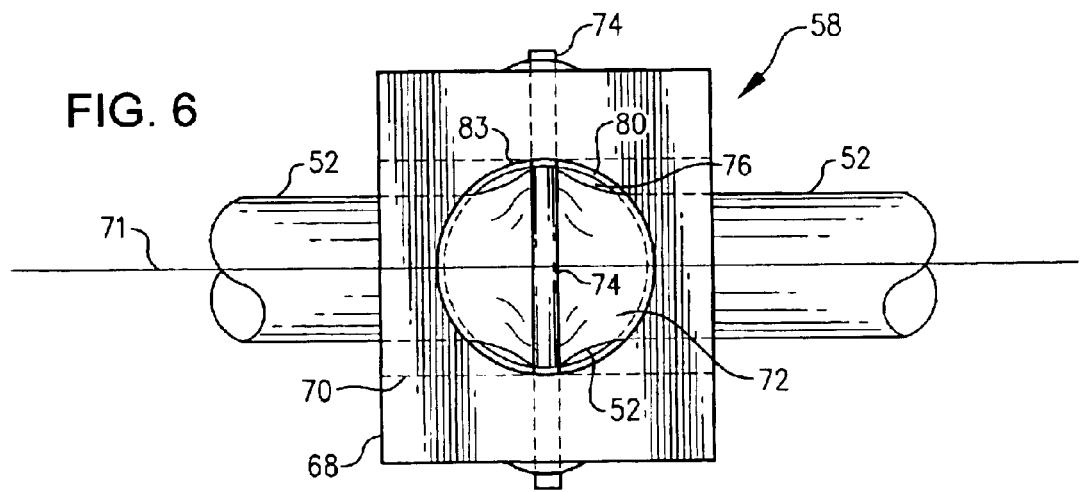
FIG. 6 is an end view of the valve of FIGS. 4 and 5 and taken along the line 6—6 in FIG. 5.

FIG. 6 is an end view of the valve 58 of FIG. 5 taken along the line 6—6 in FIG. 5. As can be seen in FIG. 6, the size of the bar 74 that contacts the drain tube 52 is significantly less than the drain-tube-contact surface 80 of the plunger 76. This allows the bar 74 to focus the pinching force of the plunger 76 and thus reduce the amount of pinching force required to close the valve 58. In addition, FIG. 6 shows the open end 84 of the valve body's cavity 72 that permits easy removal of the plunger 76, spring 78 in FIGS. 3 and 4 and spring adjustment plate 82 in FIGS. 3 and 4. By simply removing the bar 74 from the body 68 as previously discussed in conjunction with FIGS. 4 and 5, the components of the valve 58 disposed within the cavity can be removed to be cleaned or replaced when desired.

FIGS. 7 and 8 are side views of the caliper 60 in FIG. 3. FIG. 7 shows the caliper 60 in a locked position that keeps the valve 58 in FIGS. 3–6 open. FIG. 8 shows the caliper 60 in an unlocked position that closes the valve 58.

In this and certain other embodiments, the caliper 60 includes a body 86, a main lever 88 for opening and closing the valve 58, and a lock lever 90 for locking the valve 58 open. The main lever 88 is pivotally attached to the body 86 at a first location 90 using conventional techniques such as a pin and snap ring. The caliper end 66 of the cable 62 is attached to the lock lever 90 at a second location 94, as previously discussed elsewhere herein. The lock lever 90 is pivotally attached using conventional techniques to the main lever 88 at a third location 96 that does not align with the cable 62 and second location. Thus, pivotal movement of the main lever 88 causes the lock lever to pivot about the third location 96.

Still referring to FIGS. 7 and 8 in this and certain other embodiments, to open the valve 58, a user rotates the main lever 88 away from the lock lever 90 causing the main lever 88 to rotate about the first location 92. With the cable 62 attached to the plunger 76 in FIGS. 4 and 5 the plunger 76 is urged toward the open position. But, the spring 78 resists such movement causing the lock lever 90 to rotate in a direction opposite the main lever 88. After the lock lever 90 has sufficiently rotated to the locking position, it stops rotating relative to the main lever 88. Further rotation of the main lever 88 will not cause the lock lever 90 to rotate, but instead, further open the valve 58 by pulling the plunger 76 against the spring 78. Once, the valve 58 is opened, the user releases the main lever 88 to allow the lock lever 90 to contact the body 86 of the caliper 60 and retain the plunger 76 in the open position. Thus, the user does not have to hold the main lever 88 down to keep the valve 58 open. And, by extending the length of the main lever 88, one can further reduce the force required to open the valve 58.

Still referring to FIGS. 7 and 8, in this and certain other embodiments, to close the valve 58 after the valve 58 has been locked open, the user pushes the lock lever 90 toward the main lever 88. This causes the lock lever 90 to lose contact with the body 86. Once contact is lost, pushing the lock lever 90 toward the main lever causes the lock lever 90 to rotate out of the locking position. Consequently, the spring 78 pulls the main lever 88 and lock lever 90 toward the main body 86, and the plunger 76 can be moved to the closed position. By extending the length of the lock lever 90, one can reduce the strength required to close the valve 58.

Thus, to open the valve 58 and release the lock lever 90 from the locked position, a user rotates the main lever 88 and lock lever 90, respectively, in the same direction. This can be desirable when a user has some strength moving a part of his/her body in one direction but no strength in the opposite direction. For example, some quadriplegics have considerable strength extending their arm away from their body but very little strength retracting their arm back to their body.

Still referring to FIGS. 7 and 8, in this and certain other embodiments, the lock lever 90 includes a lip 98 for retaining the lock lever 90 in the locked position and a foot 100 for preventing rotation of the lock lever beyond the locked position. The lip 98 is configured to maintain contact with the body 86 to unlock the caliper 60 when the caliper 60 locks open the valve 58 yet allow rotation of the lock lever 90 toward the main lever 88. In other embodiments, the lock lever 90 can include other means for retaining the lock lever 90 in the locked position. For example, the lock lever 90 can include a groove for receiving a lip on the body 86 to lock the valve 58 open. Furthermore, the lock lever 90 can include other means for preventing rotation of the lock lever 90 beyond the locked position. For example, the main lever 88 can include a protrusion that contacts the lock lever 90 when the lock lever 90 is in the locked position.

Although a valve assembly and method for controlling the flow of fluid through a tube has been described in considerable detail with reference to certain embodiments for purposes of illustration, other embodiments are possible. Therefore the spirit and scope of the appended claims should not be limited to the above description of the embodiments; the present invention includes suitable modifications as well as all permutations and combinations of the subject matter set forth herein.

What is claimed is:

1. A valve for controlling the flow of a fluid through a tube comprising:
    a valve body including a passage having a longitudinal axis and sized to receive the tube, and a cavity that opens into the passage and includes a closed end;
    a bar attached to the body and extending through the passage adjacent the longitudinal axis and opposite the cavity;
    a plunger movable within the cavity away from the bar to an open position where the fluid can flow through the tube, and toward the bar to a closed position where the plunger pinches a portion of the tube against the bar to prevent or substantially prevent the flow of fluid through the tube;
    a spring disposed within the cavity between the closed end and the plunger and operable to bias the plunger toward the bar;
    a spring adjustment plate disposed between the closed end of the cavity and the spring and movable within the cavity to adjust the spring compression when the plunger is in the closed position; and
    a spring adjustment member operable to move the spring adjustment plate.

2. The valve of claim 1 wherein the cavity includes a longitudinal axis that is perpendicular or substantially perpendicular to the longitudinal axis of the passage.

3. The valve of claim 1 wherein the bar is straight or substantially straight and cylindrical or substantially cylindrical.

4. The valve of claim 1 wherein the bar extends in a direction perpendicular or substantially perpendicular to the longitudinal axis.

5. The valve of claim 1 wherein the plunger includes a circular plate having a drain-tube contact surface that includes at least one of the group consisting of a flat or substantially flat surface, a portion that is concave and a portion that is convex.

6. The valve of claim 1 wherein the spring includes a coil spring disposed within the cavity and compressed between the plunger and the closed end of the cavity when the plunger is in the closed position.

7. The valve of claim 1 wherein the spring adjustment member includes a screw threaded through the body to contact the spring adjustment plate.

8. The valve of claim 1 wherein the body is made of acrylonitrile butadiene styrene plastic.

* * * * *